US00PP35353P2

(12) United States Plant Patent
Robinson et al.

(10) Patent No.: US PP35,353 P2
(45) Date of Patent: Aug. 29, 2023

(54) ***STYRAX* PLANT 'RNI-RIXRED'**

(50) Latin Name: *Styrax japonicus*
Varietal Denomination: RNI-Rixred

(71) Applicant: Robinson Nursery, Inc., McMinnville, OR (US)

(72) Inventors: Joshua Ryan Robinson, McMinnville, OR (US); Christopher Lee Robinson, McMinnville, OR (US)

(73) Assignee: Robinson Nursery, Inc., McMinnville, OR (US)

( * ) Notice: Subject to any disclaimer, the term of this patent is extended or adjusted under 35 U.S.C. 154(b) by 0 days.

(21) Appl. No.: 17/845,405

(22) Filed: Jun. 21, 2022

(51) Int. Cl.
*A01H 5/00* (2018.01)
*A01H 6/00* (2018.01)

(52) U.S. Cl.
USPC ..... Plt./226

(58) Field of Classification Search
USPC ..... Plt./226
See application file for complete search history.

*Primary Examiner* — Karen M Redden
(74) *Attorney, Agent, or Firm* — Cassandra Bright

(57) ABSTRACT

A new and distinct cultivar of *Styrax* plant named 'RNI-RIXRED' is disclosed, characterized by dark, glossy foliage with emerging new growth colored bronze. Flowers bloom twice per year, in spring and again in fall. Petite, white flowers have a shiny quality. The new variety is a *Styrax*, normally used for outdoor ornamental purposes.

3 Drawing Sheets

Figure 1:
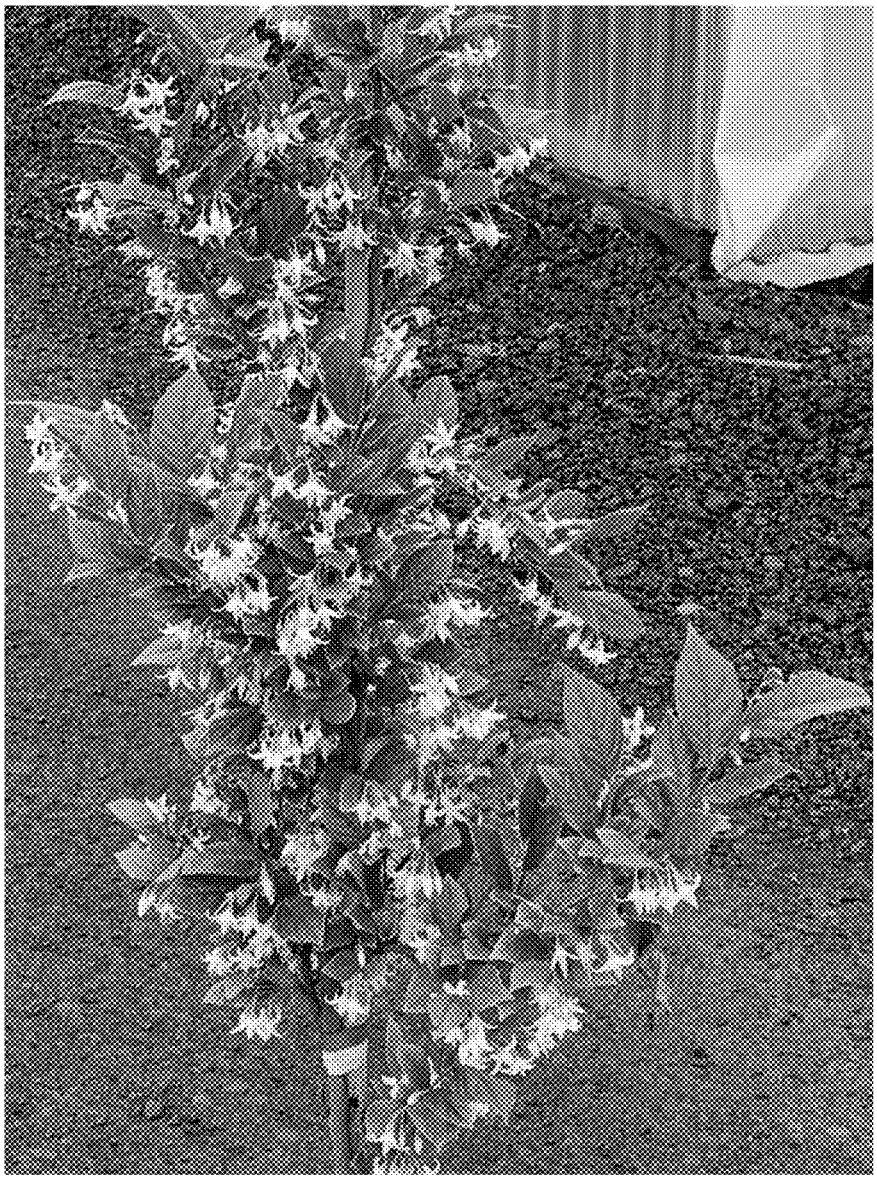

Latin name of the genus and species: *Styrax japonicus*.
Variety denomination: 'RNI-RIXRED'.

BACKGROUND OF THE INVENTION

The new *Styrax* cultivar is a product of a planned breeding program conducted by the inventor in Amity, Oreg. The objective of the breeding program was to develop an easy to propagate cultivar with a dense growth habit, and attractive foliage and flowers. The new variety is the result of open pollination occurring during the summer of 2013.

The seed parent is an unnamed variety of *Styrax japonicus*. The pollen parent is unidentified. The new variety was selected on Jul. 1, 2014, by the inventor in a group of seedlings resulting from the open pollination, in a commercial nursery in Amity, Oreg.

Asexual reproduction of the new cultivar has been performed by rooted cutting. This was first performed at a commercial nursery in Amity, Oreg., Jun. 14, 2015, and has shown that the unique features of this cultivar are stable and reproduced true to type in multiple successive generations.

The cultivar 'RNI-RIXRED' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'RNI-RIXRED' These characteristics in combination distinguish 'RNI-RIXRED' as a new and distinct *Styrax* cultivar:

1. Dark green, glossy foliage.
2. New growth emerges bronze.
3. Strong rooting with a 95-100% success rate.
4. Upright habit.
5. Flowers twice a year; once in spring, and once in fall.
6. Petite, shiny flowers.

PARENT COMPARISON

Plants of the new cultivar 'RNI-RIXRED' are comparable to the parent variety *Styrax japonica*. The two *Styrax* varieties are similar in most horticultural characteristics; however, the new variety 'RNI-RIXRED' differs in the following:

1. The new variety has a more compact habit than the seed parent.
2. New foliage growth of the new variety is bronze, while new foliage growth of the seed parent is green.
3. Flowers of the new variety are shiny, while flowers of the seed parent are matte.
4. The new variety can be consistently propagated as a rooted cutting. The seed parent does not reliably root as a cutting.
5. Foliage of the new variety is dark green, glossy, and thick, while foliage of the seed parent is light green with no gloss, and thinner.

COMMERCIAL COMPARISON

Plants of the new cultivar 'RNI-RIXRED' are comparable to the commercial variety *Styrax* 'SJMTF', U.S. Plant Pat No. 31,851. The two *Styrax* varieties are similar in most horticultural characteristics; however, the new variety 'RNI-RIXRED' differs in the following:

1. Crown of the new variety is ovate while the crown of this comparator is rounded to broad-rounded.
2. Lateral branches of the new variety begin lower on the trunk than lateral branches of this comparator.
3. New leaf flush of the new variety is bronze, while new leaf flush of this comparator is green.
4. Petals of the new variety have a shiny quality not found on petals of this comparator.

BRIEF DESCRIPTION OF THE PHOTOGRAPHS

Figure 2:
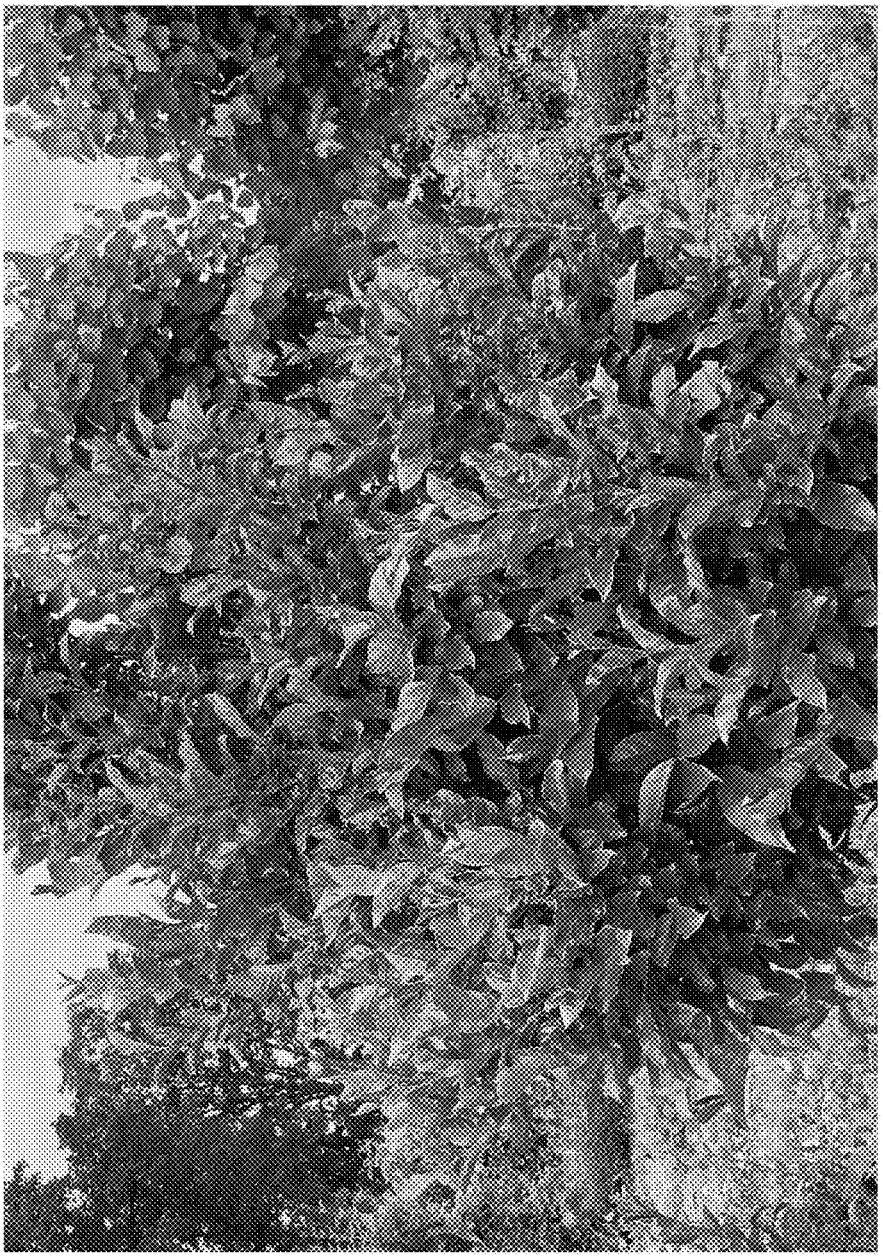

The accompanying photograph in FIG. 1 illustrates a flowering plant outdoor in a 5 gallon pot at approximately 4 years old FIG. 2 illustrates in full color a typical plant of 'RNI-RIXRED' in a trial field in Grand Haven, Mich. at approximately 6 years old.

Figure 3:
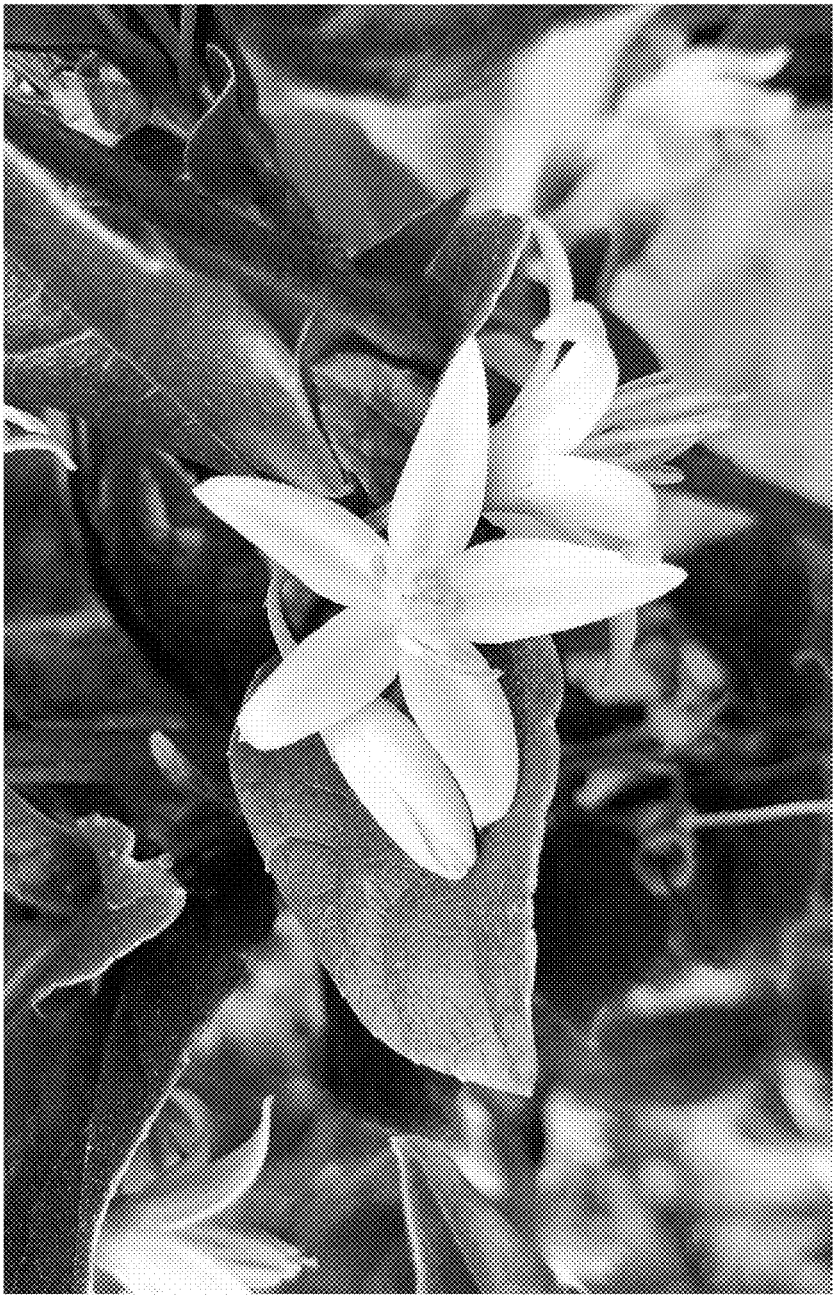

FIG. 3 illustrates a close-up of the flowers.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015 except where general terms of ordinary dictionary significance are used. The following observations and measurements describe 'RNI-RIXRED' plants grown in a poly-house in Grand Haven, Mich. The growing temperature ranged from approximately 18° C. to 27° C. during the day and from approximately 5° C. to 10° C. during the night. General light conditions are normal sunlight and numerical values represent averages of typical plant types.

Botanical classification: *Styrax japonicus* 'RNI-RIXRED'.

PROPAGATION

Type of propagation typically used: Rooted cutting.
Time to initiate roots: 2 weeks.
Time to produce a rooted cutting: 1 month to fill out a band pot during winter.
Root description: Thin, dense, fibrous, freely branching. White in color, not accurately measured with R.H.S. Chart.

PLANT

Plant type: Perennial tree.
Age of the tree described: Approximately 5 years.
Container size: 10-gallon container.
Overall plant shape: Upright small tree with an ovate canopy.
Growth habit: Upright.
Plant vigor: Moderate.
Canopy density: Dense.
Tree spread: 100 cm.
Tree height: 195 cm.
Growth rate: Approximately 6 years to reach 7 feet.
Branching characteristics: Branches alternatingly along main trunk starting 7 to 25 cm from soil level.
Length of primary lateral branches: Approximately 100 cm.
Diameter of lateral branches: Approximately 1 cm.
Approx. quantity of lateral branches: 10 to 15.
Angle of lateral branches from main trunk: 20 to 45 degrees.
Trunk:
- *Diameter*.—Approximately 1.5 cm, after 4 years, measured at 10 cm in height.
- *Texture*.—Coarse, slightly peeling.
- *Color*.—Near RHS Grey-Brown 199C and 199D Internode length: 2.5 cm.

FOLIAGE

Leaf:
- *Arrangement*.—Alternate, single.
- *Average length*.—6 to 7 cm.
- *Average width*.—3 cm.
- *Shape of blade*.—Oblanceolate.
- *Aspect*.—Slightly reflexed and very slightly undulate.
- *Apex*.—Acuminate.
- *Base*.—Obtuse.
- *Margin*.—Slightly serrulate.
- *Texture of top surface*.—Smooth, with pronounced venation.
- *Texture of bottom surface*.—Smooth, with pronounced venation.
- *Color*.—Young foliage upper side: Newest growth — RHS Greyed-Orange 166A. Young growth — RHS Brown 200A. Young foliage under side: Newest growth — RHS Greyed-Orange 166A. Young growth — RHS Brown N200A. Mature foliage upper side: RHS Yellow-Green 146B. Mature foliage under side: RHS Yellow-Green 146B.
- *Venation*.—Type: Pinnate. Venation color upper side: RHS Yellow-Green 146B. Venation color under side: RHS Yellow-Green 146B.
- *Petiole*.—Length: 1 cm. Diameter: 2 mm. Texture, upper side: Smooth. Texture, under side: Smooth. Color, upper side: RHS Yellow-Green 146B. Color, under side: RHS Yellow-Green 146B.

FLOWER

Natural flowering season: May-June, September-October.
Flowers:
- *Arrangement*.—Single axillary flowers in small groups of 8 to 10.
- *Type*.—Single flowers on axillary branches.
- *Quantity of flowers per lateral stem*.—40 to 50.
- *Quantity of buds per lateral stem*.—40 to 50.
- *Quantity of flowers and buds per plant*.—750 to 1000.
- *Diameter*.—2 cm.
- *Length*.—2 cm.
- *Depth*.—1 cm.
- *Aspect*.—Drooping.
- *Shape*.—Bell-shaped with 5 curling petals arranged in a whorl.
- *Persistence*.—Self-cleaning.
- *Fragrance*.—Sweet and floral.

Petals:
- *Arrangement*.—Star-like, whorled around base.
- *Appearance*.—Soft and silky.
- *Number*.—5.
- *Shape*.—Lanceolate.
- *Margin*.—Entire.
- *Tip shape*.—Acute.
- *Base shape*.—Fused.
- *Length*.—12 mm.
- *Width*.—4 mm.
- *Texture*.—Upper: Soft and silky. Lower: Soft and silky.
- *Color*.—When opening: Upper surface: RHS White NN155C. Under surface: RHS White NN155C. Fully opened: Upper surface: RHS White NN155C. Under surface: RHS White NN155C.

Bud:
- *Shape*.—Egg-shaped.
- *Length*.—4 to 5 mm.
- *Diameter*.—3 mm.
- *Color*.—RHS Green 138B with Yellow-Green 147D at tips.

Sepals:

*Appearance*.—Diminutive.
*Arrangement*.—Whorl.
*Number*.—5.
*Shape*.—Triangular.
*Tip*.—Acute.
*Base*.—Fused.
*Margin*.—Entire.
*Length*.—1 mm.
*Width*.—1 mm.
*Texture, upper side*.—Smooth.
*Texture, under side*.—Smooth.
*Color, upper side*.—RHS Yellow-Green 147D, fading to Green 138B.
*Color, under side*.—RHS Yellow-Green 147D, fading to Green 138B.

Calyx:

*Shape*.—Collar-like, cupping base of flower.
*Length*.—6 mm.
*Diameter*.—3 mm.
*Color*.—RHS Yellow-Green 147D Peduncle:

*Length*.—12 mm.
*Diameter*.—1 mm.
*Texture*.—Velvety.
*Color*.—RHS Green 138B.
*Strength*.—Good, flexible.
*Angle*.—30° to 45°.
*Pedicel*.—None.

REPRODUCTIVE ORGANS

Stamens:

*Number*.—9 to 10.
*Filament length*.—5 mm.
*Filament color*.—RHS White NN155C.

Anthers:

*Shape*.—Linear.
*Length*.—4 mm.
*Color*.—RHS Greyed-Yellow 162A.
*Pollen*.—Amount: Plentiful. Color: RHS Greyed-Yellow 162A.

Pistil:

*Number*.—1.
*Length*.—10 mm.
*Style*.—Length: 9 mm. Color: RHS White NN155C. Ovary Color: RHS White NN155C.

Stigma:

*Shape*.—Round.
*Color*.—RHS Greyed-Yellow 162A.

Other flower characteristics: Petals have a slight sparkling quality; two flowering periods (May-June, September-October).

OTHER CHARACTERISTICS

Fruits and seeds: Not observed to date.

Disease/pest resistance: Neither resistance nor susceptibility to normal diseases and pests of *Styrax* observed.

Temperature range: Observed to tolerate a temperature range from −23.3° C. to 37.7° C.

What is claimed is:

1. A new and distinct cultivar of *Styrax* plant named 'RNI-RIXRED' as herein illustrated and described.

* * * * *